United States Patent
Hills et al.

(10) Patent No.: US 10,662,627 B2
(45) Date of Patent: May 26, 2020

(54) ULTRAVIOLET LIGHT TREATING WATER DISPENSATION SYSTEMS AND METHODS

(71) Applicant: THE BOEING COMPANY, Chicago, IL (US)

(72) Inventors: Karen L. Hills, Seattle, WA (US); Daniel Robert Keenan, Edmonds, WA (US); Stephen I. Philips, Mukilteo, WA (US); Richard K. Simms, Mukilteo, WA (US); Douglas Alan Brown, Edmonds, WA (US)

(73) Assignee: THE BOEING COMPANY, Chicago, IL (US)

( * ) Notice: Subject to any disclaimer, the term of this patent is extended or adjusted under 35 U.S.C. 154(b) by 518 days.

(21) Appl. No.: 15/237,710

(22) Filed: Aug. 16, 2016

(65) Prior Publication Data

US 2018/0051447 A1 Feb. 22, 2018

(51) Int. Cl.
| | |
|---|---|
| *C02F 1/32* | (2006.01) |
| *E03C 1/04* | (2006.01) |
| *A61L 2/10* | (2006.01) |
| *E03C 1/046* | (2006.01) |
| *B64D 11/02* | (2006.01) |

(52) U.S. Cl.
CPC .............. *E03C 1/0404* (2013.01); *A61L 2/10* (2013.01); *C02F 1/325* (2013.01); *E03C 1/046* (2013.01); *B64D 11/02* (2013.01); *C02F 2201/001* (2013.01); *C02F 2201/3222* (2013.01); *C02F 2303/04* (2013.01); *C02F 2307/06* (2013.01)

(58) Field of Classification Search
CPC .. C02F 1/78; C02F 1/325; C02F 1/008; C02F 2103/42; C02F 2201/326; C02F 2209/40; C02F 2209/02; C02F 1/00; C02F 2103/002; C02F 2201/009; C02F 2201/3222; C02F 2209/44; C02F 2307/06; A61L 2/202; A61L 2202/11; A61L 2/20; Y02A 20/212; E03C 2201/40; Y02W 10/37
See application file for complete search history.

(56) References Cited

U.S. PATENT DOCUMENTS

| | | | |
|---|---|---|---|
| 4,819,276 A | 4/1989 | Stevens | |
| 5,853,572 A * | 12/1998 | Kuennen | C02F 9/005 210/87 |
| 7,429,742 B1 * | 9/2008 | Schweitzer | C02F 1/325 210/748.11 |
| 7,641,790 B2 * | 1/2010 | Maiden | A45F 3/20 210/91 |
| 8,421,032 B2 * | 4/2013 | Dornseifer | C02F 1/325 250/436 |
| 8,872,130 B1 * | 10/2014 | Matthews | C02F 1/325 250/455.11 |

(Continued)

FOREIGN PATENT DOCUMENTS

| | | | |
|---|---|---|---|
| CN | 201002985 Y * | 1/2008 | |
| WO | WO 2014036217 | 3/2014 | |

*Primary Examiner* — Cameron J Allen
(74) *Attorney, Agent, or Firm* — The Small Patent Law Group LLC; Joseph M Butscher

(57) ABSTRACT

A water dispensation system includes a water dispenser including a water conduit defining a water channel between a water inlet and a water outlet. A light emitter is coupled to the water conduit proximate to the water outlet. The light emitter is configured to emit sanitizing light into water that passes out of the water outlet.

20 Claims, 6 Drawing Sheets

(56) References Cited

U.S. PATENT DOCUMENTS

| | | | |
|---|---|---|---|
| 2010/0122946 A1* | 5/2010 | Staschik | C02F 1/325 |
| | | | 210/98 |
| 2011/0215037 A1* | 9/2011 | Cassassuce | B01D 35/14 |
| | | | 210/95 |
| 2011/0240566 A1* | 10/2011 | Engelhard | B01D 53/885 |
| | | | 210/748.1 |
| 2012/0261349 A1* | 10/2012 | Kolstad | C02F 1/32 |
| | | | 210/695 |
| 2014/0115764 A1 | 5/2014 | Cheng | |
| 2014/0166590 A1* | 6/2014 | Rozenberg | C02F 1/008 |
| | | | 210/746 |

* cited by examiner

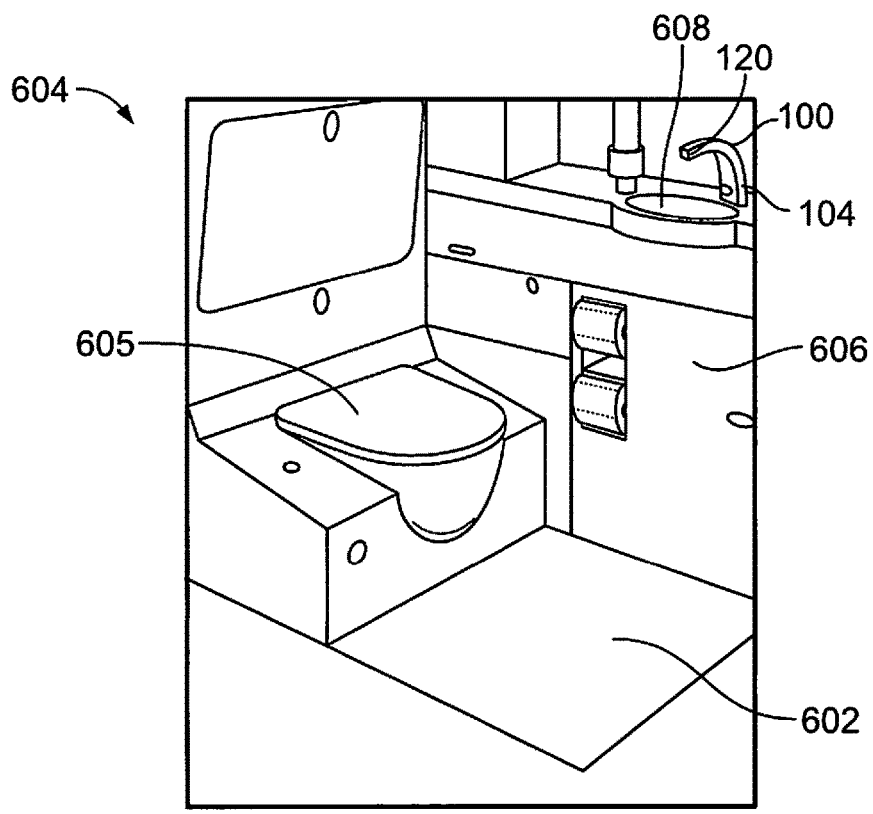
FIG. 7
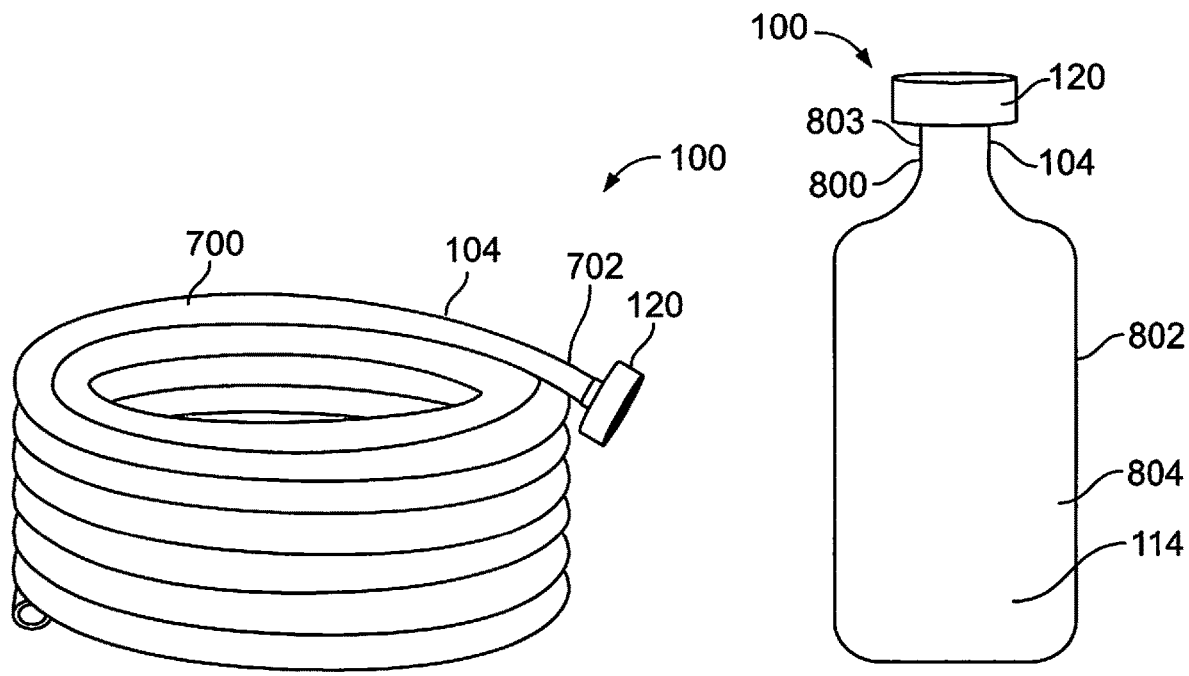
FIG. 8
FIG. 9

ULTRAVIOLET LIGHT TREATING WATER DISPENSATION SYSTEMS AND METHODS

FIELD OF THE DISCLOSURE

Embodiments of the present disclosure generally relate to systems and methods of using ultraviolet light to treat water that flows out of water dispensers.

BACKGROUND OF THE DISCLOSURE

A water-dispensing conduit includes an orifice or nozzle region that typically retains a limited amount of water after the flow of water from the water-dispensing conduit has stopped. For example, as an individual uses a faucet to wash his/her hands, a valve is actuated after use to stop the flow of water. When the valve is in the closed position, a small amount of water is often retained within the tip of the faucet. The retained water within the faucet tip is typically one or more droplets, a meniscus, or the like.

Contaminants within a surrounding environment may be introduced into the retained water. For example, germs or bacteria may be introduced into water retained within a faucet tip. During a subsequent use of the faucet, the retained water including the contaminants passes out of the faucet.

As can be appreciated, using even a small amount of contaminated water is undesirable. As such, many individuals choose to allow a certain amount of water to flow out of a faucet before washing hands, drinking, or the like. By doing so, however, water is wasted.

In certain environments, such as onboard an aircraft, the supply of water is limited. Therefore, allowing an initial amount of water to flow out of a faucet, such as onboard an aircraft lavatory, unnecessarily wastes the water, which may be in short supply.

SUMMARY OF THE DISCLOSURE

A need exists for a system and method for effectively sanitizing water that flows out of a water dispenser. A need exists for a system and method for sanitizing water that may be retained within a tip, nozzle, or orifice of a water dispenser before the retained water passes out of the water dispenser.

With those needs in mind, certain embodiments of the present disclosure provide a water dispensation system that includes a water dispenser (such as a faucet) including a water conduit defining a water channel between a water inlet and a water outlet. A light emitter is coupled to the water conduit proximate to the water outlet. The light emitter is configured to emit sanitizing light into water that passes out of the water outlet.

In at least one embodiment, the light emitter emits the sanitizing light as ultraviolet (UV) light. In at least one embodiment, the ultraviolet light is far UV light.

The light emitter may include at least one light emitting diode. In at least one embodiment, the light emitter includes a light-emitting ring surrounding the water outlet.

The water dispensation system may also include a valve disposed within the water channel, and a valve actuator operatively coupled to the valve. The valve actuator is configured to selectively open and close the valve. In at least one embodiment, the valve actuator is linked to the light emitter, such that the light emitter is activated when the valve actuator opens the valve, and the light emitter is deactivated when the valve actuator closes the valve.

The water dispensation system may include at least one status indicator that illuminates when the light emitter is active.

The water dispensation system may include a shroud that covers at least a portion of the light emitter. The shroud is configured to shield an environment from the sanitizing light.

In at least one embodiment, the light emitter is configured to emit the sanitizing light into the water before the water begins to flow out of the water outlet. The light emitter may be configured to intermittently emit the sanitizing light.

Certain embodiments of the present disclosure provide a water dispensation method that includes opening a valve that is disposed within a water channel of a water conduit, and emitting sanitizing light from a light emitter coupled to the water conduit proximate to a water outlet of the water channel into water that passes out of the water outlet at least one of before or when the valve is opened.

The emitting may include emitting the sanitizing light as ultraviolet (UV) light. The ultraviolet light may be far UV light.

The opening may include using a valve actuator operatively coupled to the valve to open the valve. The water dispensation method may include linking the valve actuator to the light emitter, such that the opening causes the emitting. The method may also include deactivating the light emitter when the valve actuator closes the valve.

The method may include illuminating at least one status indicator during the emitting operation.

The method may include using a shroud that covers at least a portion of the light emitter to shield an environment from the sanitizing light.

BRIEF DESCRIPTION OF THE DRAWINGS

FIG. 7 illustrates a perspective internal view of a lavatory, according to an embodiment of the present disclosure.

FIG. 8 illustrates a perspective view of a water dispensation system, according to an embodiment of the present disclosure.

FIG. 9 illustrates a lateral view of a water dispensation system, according to an embodiment of the present disclosure.

DETAILED DESCRIPTION OF THE DISCLOSURE

Figure 1:
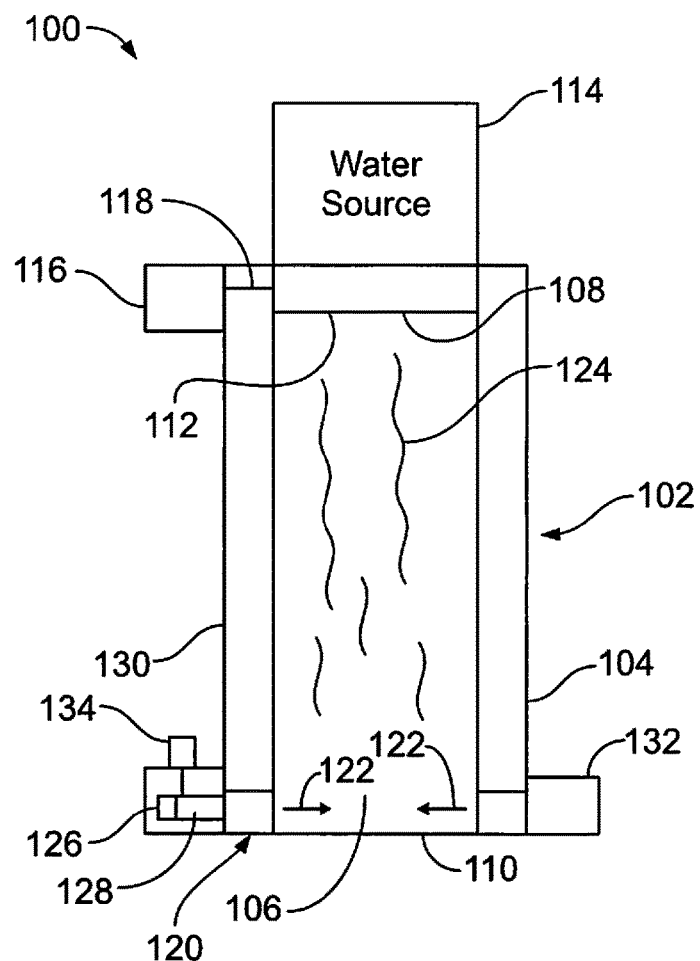
FIG. 1 illustrates a schematic diagram of a water dispensation system, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide a water dispensation system that includes a light emitter that emits sanitizing light into a water channel at a distal tip (such as an orifice, nozzle or the like). In at least one embodiment, the sanitizing light is ultraviolet light, particularly far ultraviolet light. The sanitizing light emitted into the water channel ensures that water flowing out of the water channel is clean and safe for use. The light emitter may be located at a distal tip of the water dispenser and may emit a glowing light, which indicates to a user of the water dispensation system that water flowing out of the water channel is being sanitized. The sanitizing light sanitizes the water by disinfecting, cleaning or otherwise treating the water, such as by killing or otherwise ridding microbes.

Certain embodiments of the present disclosure provide a water nozzle that includes an inwardly-facing ultraviolet (UV) light emitter proximate to an orifice of the nozzle. In at least one embodiment, the UV light emitter is configured to emit far UV light into a water channel at the orifice. The UV light emitter may emit the UV light into water flowing out of the water nozzle for as long as water flows from the water nozzle. In at least one other embodiment, the UV light emitter may emit the UV light into the water flowing out of the water nozzle for less than an entire time that water flows out of the water nozzle. For example, the UV light emitter may emit the UV light into water for the first few seconds (for example, 2 or 3 seconds) that water flows from the water nozzle.

In at least one embodiment, the UV light emitter may emit the UV light into water within the water nozzle before water begins to flow out of the water nozzle in order to ensure that water within the water nozzle is sanitized before passing out of the water nozzle. In at least one embodiment, the UV light emitter may intermittently emit UV light at regular time intervals, such as every thirty seconds. In at least one embodiment, the UV light emitter may emit UV light when an individual approaches the water nozzle (such as through one or more proximity sensors). Further, the UV light emitter may cease emitting UV light after the water flows out of the water nozzle.

The UV light emitter may be or include a UV light ring at a tip of the water dispenser. The UV light emitter may include one or more light emitting diodes (LEDs), a fiber optic light tube in the form of a ring, one or more light bulbs, and/or the like.

In at least one embodiment, the water dispenser is a faucet. The faucet may be within a lavatory onboard an aircraft, for example. In other embodiments, the water dispenser is a hose, spigot, bottle, tank, or the like.

FIG. 1 illustrates a schematic diagram of a water dispensation system 100, according to an embodiment of the present disclosure. The water dispensation system 100 includes a water dispenser 102, such as a faucet, hose, spigot, bottle, tank, or the like. The water dispenser 102 includes a water conduit 104 defining a water channel 106 extending from a water inlet 108 to a water outlet 110, such as a nozzle, orifice, or the like.

A valve 112 is positioned within the water channel 106. As shown in FIG. 1, the valve 112 may be proximate to the water inlet 108. Optionally, the valve 112 may be disposed at various other locations within the water channel 106, such as closer to the water outlet 110.

The water inlet 108 is in fluid communication with a water source 114, such as a water tank, one or more conduits connected to a source of municipal, commercial, or residential water, and/or the like. When the valve 112 is in the closed position, water from the water source 114 is blocked from passing through the water channel 106. When the valve 112 is in the open position, water supplied from the water source 114 flows into the water channel 106 and out of the water outlet 110.

The valve 112 is operatively coupled to a valve actuator 116, such as through a link 118. The link 118 may be a mechanical and/or electrical link. The valve actuator 116 may be a handle, dial, button, wheel, and/or the like. Optionally, the valve actuator 116 may be a touch sensor (such as a capacitive touch sensor) that is configured to selectively open and close the valve 112 through touching. In at least one other embodiment, the valve actuator 116 may be a proximity sensor that selectively opens and closes the valve 112 based on the presence of an object (such as a hand of an individual) within a defined detection zone. For example, the proximity sensor may detect the presence of an object through infrared signals, ultrasonic signals, motion detection, light detection, and/or the like.

A light emitter 120 is coupled to the water dispenser 102. As shown, the light emitter 120 may be located proximate to the water outlet 110, such as around and/or within the water outlet 110. The light emitter 120 is configured to emit sanitizing light 122 into the water channel 106 at the water outlet 110. In at least one embodiment, the sanitizing light 122 is UV light. In particular, the sanitizing light is far UV light, such as having a wavelength between 122-200 nanometers. Optionally, the sanitizing light may have a wavelength between 175-300 nanometers. It has been found that far UV light efficiently and safely sanitizes water 124 that passes out of the water outlet 110. Far UV light emitted into the water instantaneously or approximately instantaneously kills or otherwise rids any bacteria, germs, or other microbes that may be present within the water 124.

In at least one embodiment, the light emitter 120 includes one or more LEDs, which may be configured to emit far UV light. In at least one other embodiment, the light emitter 120 includes a fiber optic tube, one or more bulbs, and/or the like.

The light emitter 120 is coupled to a power source 126, such as a battery. In at least one other embodiment, the power source 126 may be a source of power within a building, vehicle, or the like, such as a source of alternating current (AC) power. For example, the light emitter 120 may be coupled to a source of AC power through one or more wires, traces, cables, and/or the like. In at least one other embodiment, the power source 126 may be one or more light power cells (such as solar cells), a geothermal source of power, and/or the like.

The light emitter 120 may also be coupled to a switch 128 that is configured to selectively activate and deactivate the light emitter 120. In at least one embodiment, the switch 128 is operatively coupled to the valve actuator 116 through a link 130, such as a mechanical and/or electrical link. In this manner, operation of the valve actuator 116 may be linked to operation of the light emitter 120 so that when the valve actuator 116 opens the valve 112, the light emitter 120 is activated, and when the valve actuator 116 closes the valve 112, the light emitter 120 is deactivated. In at least one other embodiment, the light emitter 120 may be configured to emit light into the water channel 106 for less than an entire time that the water 124 flows therethrough. For example, the light emitter 120 may be configured to emit light into the water channel 106 for only the first few seconds (for example, 2 or 3 seconds) that the water 124 flows through the water channel 106.

In at least one other embodiment, the switch 128 may be or otherwise coupled to a button, lever, or other such actuation device that is configured to be engaged by an individual. In this embodiment, instead of the light emitter 120 being linked to the valve actuator 116, an individual may directly activate and deactivate the light emitter 120 as desired. For example, in order to sanitize water that may be retained within the water outlet 110 before the valve actuator 116 is engaged to open the valve 112, an individual may engage the switch 128 (for example, pressing a button coupled to the switch 128) so that the light emitter 120 emits sanitizing light into the water channel 106. After the light emitter 120 is activated, the individual may then engage the valve actuator 116 to open the valve 112 to allow water to flow through the water channel 106 and out of the water outlet 110. Because the light emitter 120 was activated before the valve 112 was opened, all of the water 124 that passes out of the water outlet 110 is sanitized. The individual may then deactivate the light emitter 120 as desired.

When the light emitter 120 is activated, a glowing light may be emitted therefrom. For example, the light emitter 120 may be contained within a transparent light ring surrounding or positioned below the water outlet 110. The light emitter 120 emits the sanitizing light 122 into the water channel 106, and also glows, thereby indicating to an individual that the water flowing out of the water outlet 110 is being sanitized.

In at least one other embodiment, a shroud 132 may be positioned around outer portions of the light emitter 120. For example, the shroud 132 may be formed around outer lateral and/or upper portions of the light emitter 120. The shroud 132 may be formed from an opaque material, such as a metal or plastic, which prevents light from passing therethrough. As such, the shroud 132 is configured to block the sanitizing light 122 from being emitted into a surrounding environment. In this embodiment, the light emitter 120 may also be coupled to a status indicator light 134 (such as an LED that is configured to emit visible light) that emits light when the light emitter 120 is active. In at least one embodiment, the status indicator may be outwardly-emitted light (for example, a glow) of the light emitter 120. In at least one other embodiment, the status indicator may be a display (such as a digital display) that indicates that the light emitter 120 is active, such as through text (for example, "ON"). Optionally, the water dispensation system 100 may not include the shroud 132 and/or the status indicator light 134.

As noted, in operation, in order to sanitize the water 124 that flows out of the water outlet 110 of the water channel 106, the light emitter 120 is activated. The light emitter 120 may be linked to the valve actuator 116 and automatically activated when the water valve 112 is opened (and automatically deactivated when the water valve 112 is closed), or the light emitter 120 may be directly activated and deactivated by an individual. During activation, the light emitter 120 emits the sanitizing light 122 into the water channel 106 at or otherwise proximate to the water outlet 110, thereby sanitizing the water 124 that passes out of the water outlet 110. In at least one embodiment, the sanitizing light is far UV light, which safely, quickly, and efficiently sanitizes the water 124 that passes out of the water outlet 110.

The light emitter 120 may be integrally formed with the water dispenser 102. In at least one other embodiment, the light emitter 120 is secured to or retrofit to an existing water dispenser 102.

Figure 2:
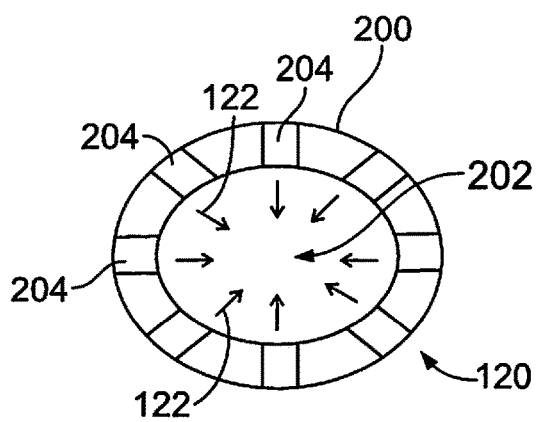
FIG. 2 illustrates a top view of a light emitter, according to an embodiment of the present disclosure.

FIG. 2 illustrates a top view of the light emitter 120, according to an embodiment of the present disclosure. In at least one embodiment, the light emitter 120 includes a bracket 200 (such as a metal or plastic ring) that securely couples to the water conduit 104 proximate to the water outlet 110. For example, the bracket 200 may secure to a bottom edge of the water conduit 104. In at least one other embodiment, the bracket 200 may be sized and shaped to fit within the water conduit 104.

The bracket 200 defines a central sanitizing passage 202. The sanitizing passage 202 provides an open channel through which water passes.

The bracket 200 supports a plurality of insulated lights 204, such as LEDs. The lights 204 may be contained within transparent plastic housings, for example, and are configured to emit the sanitizing light 122 into the sanitizing passage 202. Accordingly, as water passes through the sanitizing passage 202, the sanitizing light 122 sanitizes the water.

As shown in FIG. 2, the light emitter 120 may include a plurality of lights 204. The light emitter 120 may include more or less lights 204 than shown. In at least one embodiment, the light emitter 120 may include a single annular light that extends around (or substantially extends around) the sanitizing passage 202.

Figure 3:
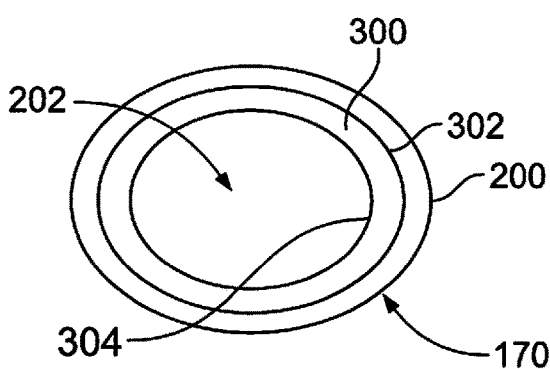
FIG. 3 illustrates of a top view of a light emitter, according to an embodiment of the present disclosure.

FIG. 3 illustrates a top view of the light emitter 120, according to an embodiment of the present disclosure. In this embodiment, the bracket 200 supports a single light 300, such as a fiber optic light within a transparent formed tube 302 surrounding the sanitizing passage 202. As shown in FIG. 3, the light emitter 120 may be or include a light-emitting ring 304 surrounding the sanitizing passage 202. In at least one embodiment, the light-emitting ring 304 surrounds the water outlet 110 (shown in FIG. 1).

Figure 4:
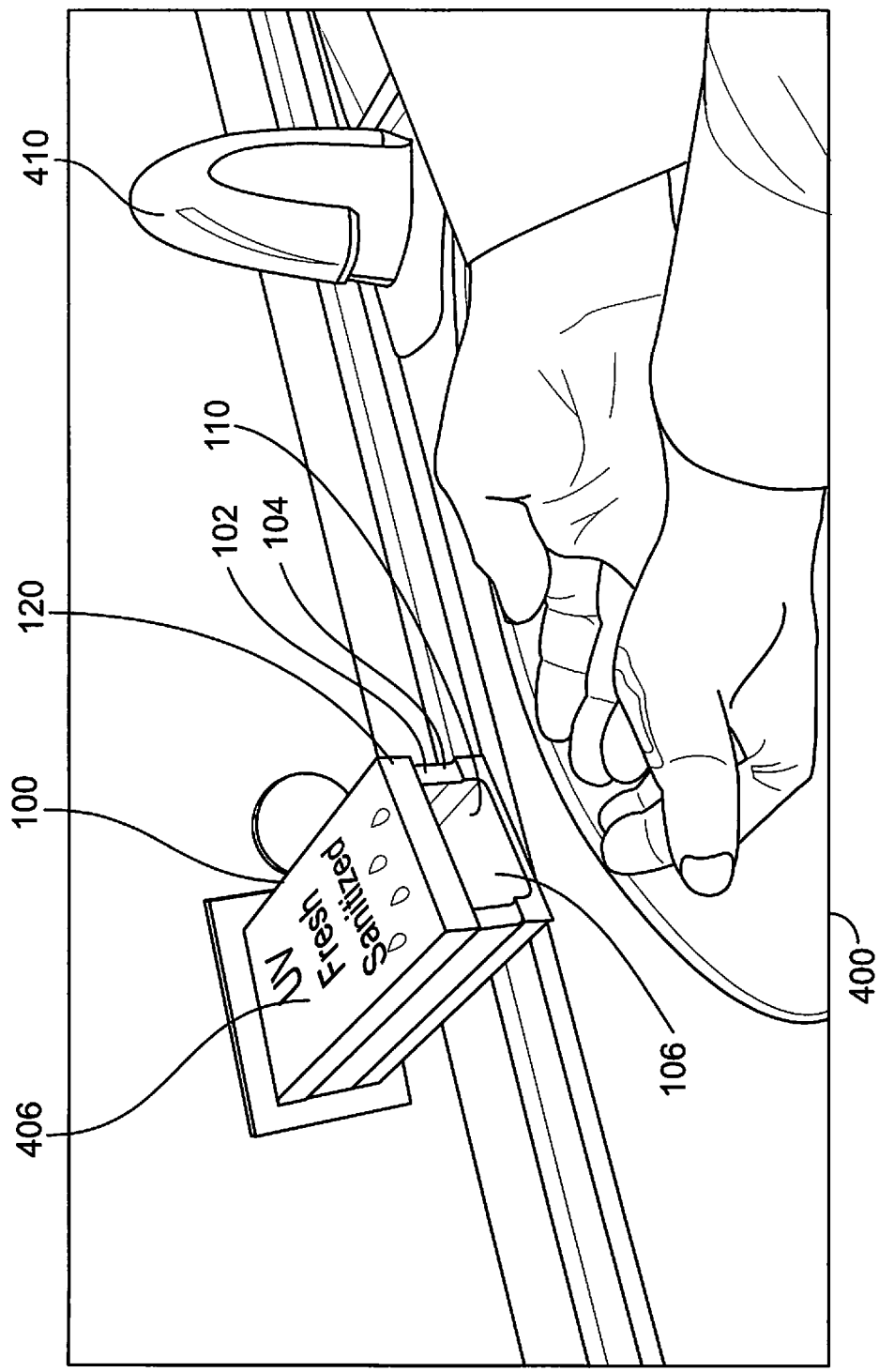
FIG. 4 illustrates a perspective view of a water dispensation system in relation to a sink, according to an embodiment of the present disclosure.

FIG. 4 illustrates a perspective view of the water dispensation system 100 in relation to a sink 400, according to an embodiment of the present disclosure. As shown, the water dispenser 102 may be a faucet in which the water outlet 110 is positioned over the sink 400. The light emitter 120 may be mounted over the water channel 106 and emit the sanitizing light downwardly into the water channel 106 when active.

The light emitter 120 may include indicia 406 (such as text) indicating that sanitized water flows out of the faucet. Further, the light emitter 120 may glow when active, thereby indicating to an individual that water flowing out of the faucet is sanitized.

As shown, another faucet 410 may be positioned proximate to the sink 400. The faucet 410 may or may not include a separate light emitter that is configured to sanitize water that flows out of the faucet 410.

The water dispensation system 100 may be utilized with respect to a faucet within a lavatory, for example. The lavatory may be within a fixed structure, or within a vehicle, such as an aircraft.

Figure 5:
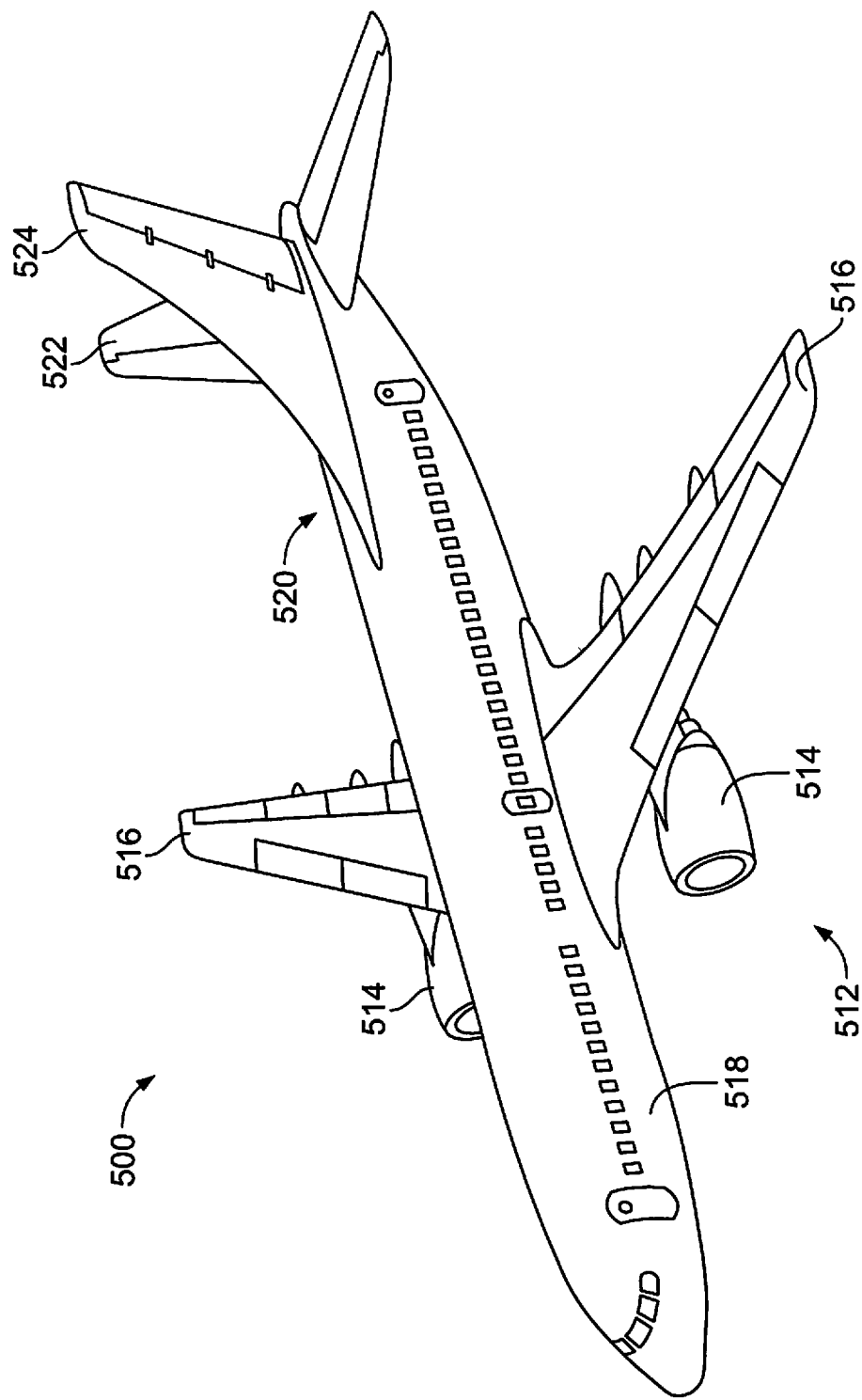
FIG. 5 illustrates a perspective top view of an aircraft, according to an embodiment of the present disclosure.

FIG. 5 illustrates a perspective top view of an aircraft 500, according to an embodiment of the present disclosure. The aircraft 500 may include one or more lavatories that utilize water dispensation systems, as described above. The aircraft 500 includes a propulsion system 512 that may include two turbofan engines 514, for example. Optionally, the propulsion system 512 may include more engines 514 than shown.

The engines 514 are carried by wings 516 of the aircraft 500. In other embodiments, the engines 514 may be carried by a fuselage 518 and/or an empennage 520. The empennage 520 may also support horizontal stabilizers 522 and a vertical stabilizer 524.

The fuselage 518 of the aircraft 500 defines an internal cabin, which may include a cockpit, one or more work sections (for example, galleys, personnel carry-on baggage areas, and the like), one or more passenger sections (for example, first class, business class, and coach sections), and an aft section in which an aft rest area assembly may be positioned. Each of the sections may be separated by a cabin transition area, which may include one or more class divider assemblies. Overhead stowage bin assemblies may be positioned throughout the internal cabin. The internal cabin includes one or more chambers, such as lavatories, for example.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 6A:
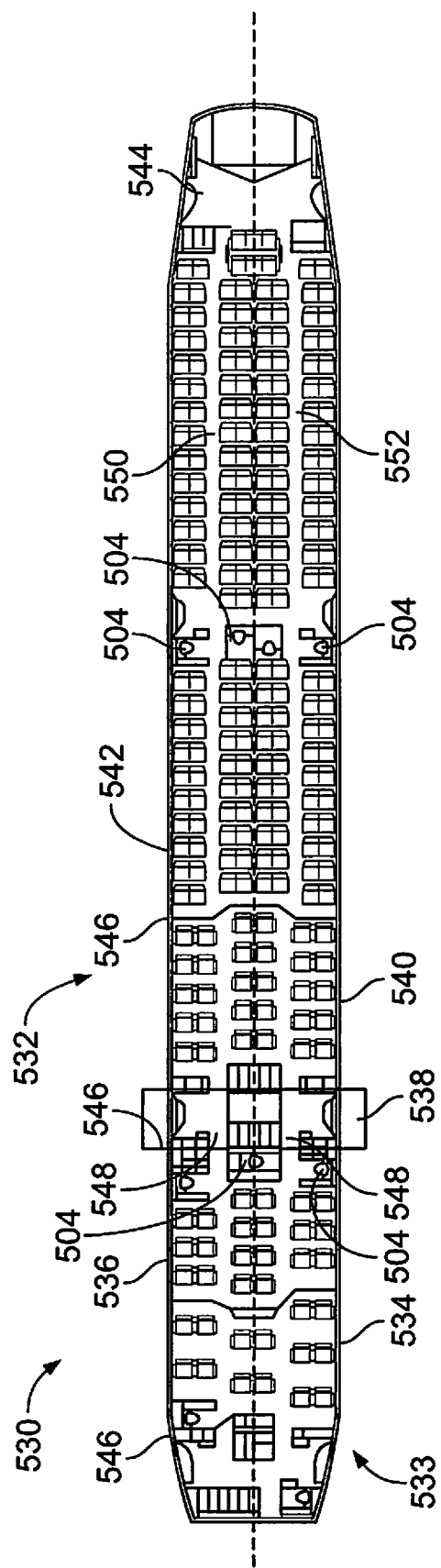
FIG. 6A illustrates a top plan view of an internal cabin of an aircraft, according to an embodiment of the present disclosure.

FIG. 6A illustrates a top plan view of an internal cabin 530 of an aircraft, according to an embodiment of the present disclosure. The internal cabin 530 may be within a fuselage 532 of the aircraft. For example, one or more fuselage walls may define the internal cabin 530. The internal cabin 530 includes multiple sections, including a front section 533, a first class section 534 (or first class suites, cabins, for example), a business class section 536, a front galley station 538, an expanded economy or coach section 540, a standard economy or coach section 542, and an aft section 544, which may include multiple chambers 504, such as lavatories and galley stations. Water dispensation systems 100 (such as shown and described with respect to FIGS. 1-4) may be positioned within one or more of the chambers 504. It is to be understood that the internal cabin 530 may include more or less sections than shown. For example, the internal cabin 530 may not include a first class section, and may include more or less galley stations than shown. Each of the sections may be separated by a cabin transition area 546, which may include class divider assemblies between aisles 548.

As shown in FIG. 6A, the internal cabin 530 includes two aisles 550 and 552 that lead to the aft section 544. Optionally, the internal cabin 530 may have less or more aisles than shown. For example, the internal cabin 530 may include a single aisle that extends through the center of the internal cabin 530 that leads to the aft section 544.

Figure 6B:
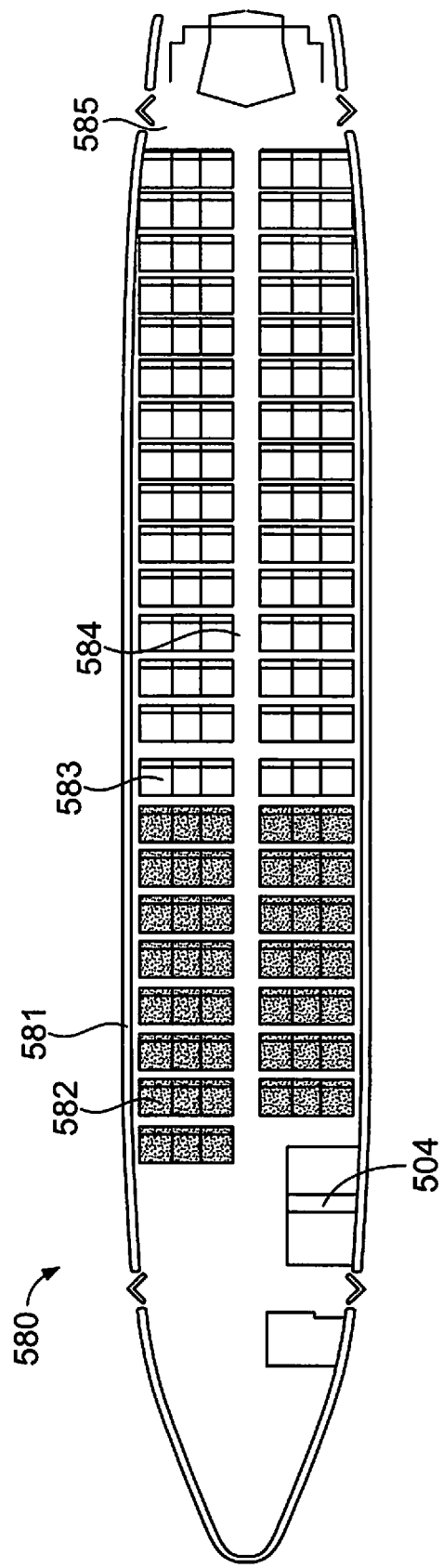
FIG. 6B illustrates a top plan view of an internal cabin of an aircraft, according to an embodiment of the present disclosure.

FIG. 6B illustrates a top plan view of an internal cabin 580 of an aircraft, according to an embodiment of the present disclosure. The internal cabin 580 may be within a fuselage 581 of the aircraft. For example, one or more fuselage walls may define the internal cabin 580. The internal cabin 580 includes multiple sections, including a main cabin 582 having passenger seats 583, and an aft section 585 behind the main cabin 582. It is to be understood that the internal cabin 580 may include more or less sections than shown.

The internal cabin 580 may include a single aisle 584 that leads to the aft section 585. The single aisle 584 may extend through the center of the internal cabin 580 that leads to the aft section 585. For example, the single aisle 584 may be coaxially aligned with a central longitudinal plane of the internal cabin 580.

One or more chambers 504, such as lavatories, may be located within the internal cabin 580. The lavatories 504 may include water dispensation systems, as described above with respect to FIGS. 1-4.

FIG. 7 illustrates a perspective internal view of a lavatory 604, according to an embodiment of the present disclosure. The lavatory 604 may be onboard an aircraft, as described above. Optionally, the lavatory 604 may be onboard various other vehicles. In other embodiments, the lavatory 604 may be within a fixed structure, such as a commercial or residential building.

The lavatory 604 includes a base floor 602 that supports a toilet 605, cabinets 606, and a sink 608. A water dispensation system 100, such as described above with respect to FIGS. 1 and 4, is positioned proximate to the sink 608. The light emitter 120 is located at a distal tip of a water conduit 104, which, in this embodiment is a faucet. As described above with respect to FIGS. 1-4, when activated, the light emitter 120 sanitizes water that passes out of the faucet.

FIG. 8 illustrates a perspective view of the water dispensation system 100, according to an embodiment of the present disclosure. In this embodiment, the water conduit 104 is a hose 700. The light emitter 120 is coupled to an outlet tip 702 of the hose 700. Water that flows out of the hose 700 is sanitized proximate to the outlet tip 702 by the light emitter 120, as described above.

FIG. 9 illustrates a lateral view of a water dispensation system 100, according to an embodiment of the present disclosure. In this embodiment, the water conduit 104 is a nozzle 800 of a water receptacle 802, such as a bottle or tank that retains water. The water source 114 is an internal chamber 804 of the water receptacle 804 that connects to the nozzle 800. The light emitter 120 is coupled to an outlet 803 of the nozzle 800. Water that flows out of the nozzle 800 is sanitized proximate to the outlet 803 by the light emitter 120, as described above.

Figure 10:
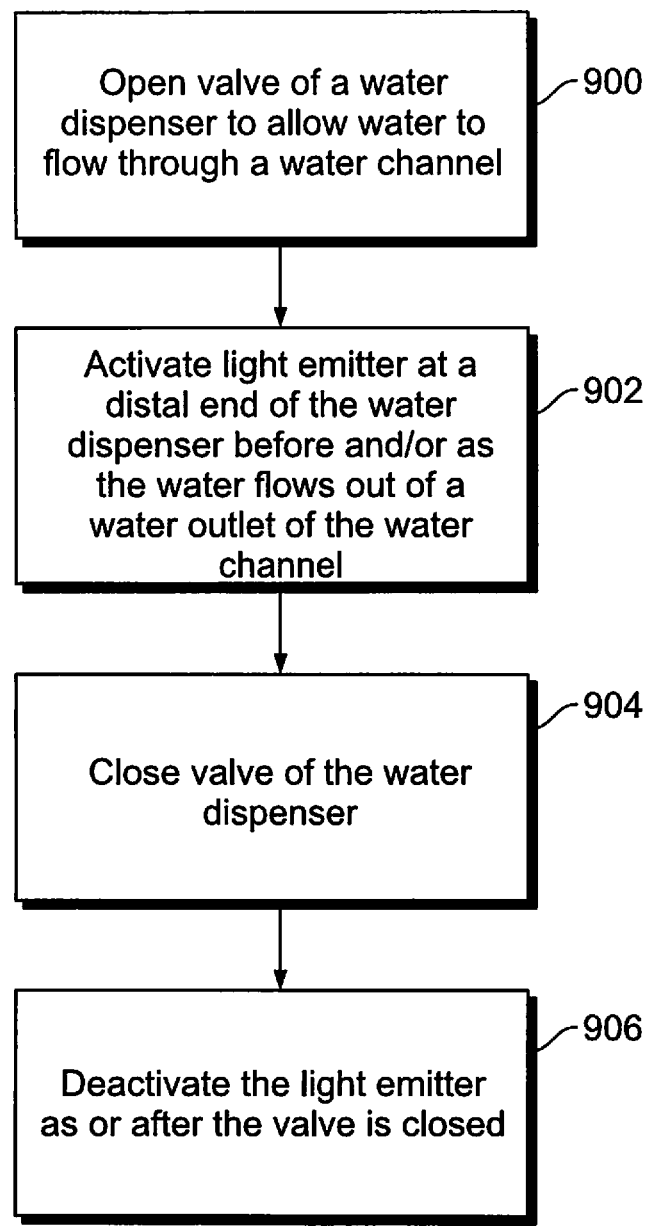
FIG. 10 illustrates a flow chart of a method of operating a water dispensation system, according to an embodiment of the present disclosure.

FIG. 10 illustrates a flow chart of a method of operating a water dispensation system, according to an embodiment of the present disclosure. At 900, a valve of a water dispenser is opened, thereby allowing water to flow through a water channel. At 902, a light emitter at a distal end of the water dispenser is activated before and/or as the water flows out of a water outlet of the water channel. The light emitter emits sanitizing light into the water as it flows out of the water outlet.

At 904, the valve of the water dispenser is closed. At 906, the light emitter is deactivated as or after the valve is closed.

As described above, embodiments of the present disclosure provide systems and methods for effectively sanitizing water that flows out of a water dispenser. Embodiments of the present disclosure provide systems and methods for sanitizing water that may be retained within a tip, nozzle, or orifice of a water dispenser before the retained water flows out of the water dispenser.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A water dispensation system, comprising:
   a water dispenser including a water conduit defining a water channel between a water inlet and a water outlet;
   a light emitter that intermittently emits sanitizing light into water that passes out of the water outlet;
   a switch coupled to the light emitter, wherein the switch selectively activates and deactivates the light emitter;
   a valve; and
   a valve actuator operatively coupled to the valve and the switch, wherein the valve actuator selectively opens and closes the valve, wherein the valve actuator is linked to the light emitter through the switch, wherein the light emitter is activated when the valve actuator opens the valve, and wherein the light emitter is deactivated when the valve actuator closes the valve.

2. The water dispensation system of claim 1, wherein the light emitter emits the sanitizing light as ultraviolet (UV) light.

3. The water dispensation system of claim 2, wherein the ultraviolet light is far UV light.

4. The water dispensation system of claim 1, wherein the water dispenser comprises a faucet.

5. The water dispensation system of claim 1, wherein the light emitter comprises at least one light emitting diode.

6. The water dispensation system of claim 1, wherein the light emitter comprises a light-emitting ring surrounding the water outlet.

7. The water dispensation system of claim 1, further comprising at least one status indicator that illuminates when the light emitter is active.

8. The water dispensation system of claim 1, further comprising a shroud that covers at least a portion of the light emitter, wherein the shroud is configured to shield an environment from the sanitizing light.

9. The water dispensation system of claim 1, wherein the light emitter is configured to emit the sanitizing light into the water before the water begins to flow out of the water outlet.

10. The water dispensation system of claim 1, wherein the light emitter intermittently emits sanitizing light into the water that passes out of the water outlet by automatically, alternately, and repeatedly activating and deactivating.

11. A water dispensation method, comprising:
    opening a valve that is disposed within a water channel of a water conduit, wherein the opening comprises using a valve actuator operatively coupled to the valve to open the valve;
    emitting sanitizing light from a light emitter coupled to the water conduit proximate to a water outlet of the water channel into water that passes out of the water outlet at least one of before or when the valve is opened, wherein the emitting the sanitizing light comprises intermittently emitting the sanitizing light;
    linking the valve actuator to the light emitter through a switch that is coupled to the light emitter and the valve actuator, wherein the opening causes the emitting; and
    deactivating the light emitter when the valve actuator closes the valve.

12. The water dispensation method of claim 11, wherein the emitting comprises emitting the sanitizing light as ultraviolet (UV) light.

13. The water dispensation method of claim 11, wherein the ultraviolet light is far UV light.

14. The water dispensation method of claim 11, further comprising illuminating at least one status indicator during the emitting operation.

15. The water dispensation method of claim 11, further comprising using a shroud that covers at least a portion of the light emitter to shield an environment from the sanitizing light.

16. The water dispensation method of claim 11, wherein the intermittently emitting the sanitizing light comprises automatically, alternately, and repeatedly activating and deactivating the light emitter as the water passes out of the water outlet.

17. A water dispensation system, comprising:
    a water dispenser including a water conduit defining a water channel between a water inlet and a water outlet;
    a valve disposed within the water channel;
    a valve actuator operatively coupled to the valve, wherein the valve actuator selectively opens and closes the valve;
    a switch coupled to the valve actuator;
    a light emitter coupled to the switch and the water conduit proximate to the water outlet, wherein the light emitter intermittently emits sanitizing far ultraviolet (UV) light into water that passes out of the water outlet, wherein the valve actuator is linked to the light emitter through the switch, wherein the light emitter is activated when the valve actuator opens the valve, and wherein the light emitter is deactivated when the valve actuator closes the valve; and at least one status indicator that illuminates when the light emitter is active.

18. The water dispensation system of claim 17, wherein the light emitter comprises one or more of a light emitting diode, or a light-emitting ring surrounding the water outlet.

19. The water dispensation system of claim 17, further comprising a shroud that covers at least a portion of the light emitter, wherein the shroud is configured to shield an environment from the sanitizing light.

20. The water dispensation system of claim 17, wherein the light emitter intermittently emits sanitizing light into the water that passes out of the water outlet by automatically, alternately, and repeatedly activating and deactivating.

* * * * *